(12) United States Patent
Wang et al.

(10) Patent No.: US 6,642,384 B1
(45) Date of Patent: Nov. 4, 2003

(54) PREPARATION OF CHIRAL 1,2,3,4-TETRAHYDRO-6,7-DIALKOXY-3-ISOQUINOLINECARBOXYLIC ACID AND DERIVATIVES

(75) Inventors: Zhi-Xian Wang, Brantford (CA); Stephen E. Horne, Burlington (CA)

(73) Assignee: Brantford Chemicals Inc., Brantford (CA)

(*) Notice: Subject to any disclaimer, the term of this patent is extended or adjusted under 35 U.S.C. 154(b) by 0 days.

(21) Appl. No.: 10/166,102

(22) Filed: Jun. 11, 2002

(30) Foreign Application Priority Data

May 31, 2002 (CA) .............................................. 2388475

(51) Int. Cl.⁷ ........................................... C07D 217/12
(52) U.S. Cl. ......................................... 546/147; 546/80
(58) Field of Search ...................................... 546/147.8

(56) References Cited

U.S. PATENT DOCUMENTS

| | | | |
|---|---|---|---|
| 3,669,837 A | 6/1972 | Parcell ......................... | 195/29 |
| 4,344,949 A | 8/1982 | Hoefle et al. ............... | 424/258 |
| 4,912,221 A | 3/1990 | O'Reilly et al. ........... | 546/147 |

FOREIGN PATENT DOCUMENTS

| | | | | |
|---|---|---|---|---|
| DE | 2 148 953 | 4/1972 | ......... | C07C/101/30 |
| GB | 1 241 405 | 8/1971 | ......... | C07C/101/30 |
| WO | WO 01/70269 A1 * | 9/2001 | ......... | A61K/45/00 |

OTHER PUBLICATIONS

Brossi, A., et al., *'Alkaloids 'in Mammalian Tissues. I. Condensation of L–Dopa and its two Mono–O–methyl Ethers with Formaldehyde and Acetaldehyde*, Helv. Chim. Acta, vol. 55, 1972, pp. 15–21.

Greene, T. W. and Wuts, P. G. M., *Protection for the Amino Group*, Protective Groups in Organic Synthesis, Chapter 7, Second Edition, John Wiley & Sons, Inc., 1999, pp. 494–653.

Klutchko, S., et al, *Synthesis of Novel Angiotensin Converting Enzyme Inhibitor Quinapril and Related Compounds. A Divergence of Structure–Activity Relationships for Non–Sulrhydryl and Sulrhydryl Types*, J. Med. Chem., vol. 29, 1986, pp. 1953–1961.

Shah, R. J., et al., *Heterocyclic Compounds. I. Synthesis of Some Isoquinoline Derivatives*, J. Org. Chem., 1961, 26, pp. 3533–3534.

* cited by examiner

*Primary Examiner*—Zinna Northington Davis
(74) *Attorney, Agent, or Firm*—Marcelo K. Sarkis; Kitt Sinden; Ivor M. Hughes

(57) ABSTRACT

The present invention relates to a process for the production of (S)-1,2,3,4-tetrahydro-6,7-dialkoxy-3-isoquinolinecarboxylic acid compounds (1) and their derivatives from Levodopa (L-Dopa). The ultimately prepared compounds are used as intermediates for, but not limited to, the preparation of substituted derivatives of 1,2,3,4-tetrahydro-6,7-dialkoxy-3-isoquinolinecarboxylic acid

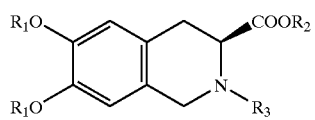

wherein $R_1$ is hydrogen, lower alkyl, C2–C12 acyl, or R1O together are methylenedioxy;

$R_2$ is hydrogen, alkyl, substituted alkyl, alkenyl, substituted alkenyl, aryl, substituted aryl, aralkyl or substituted aralkyl group; and $R_3$ is hydrogen, C2–C12 acyl group, benzyl, alkoxylcarbonyl group, or aralkoxyl carbonyl group.

10 Claims, No Drawings

PREPARATION OF CHIRAL 1,2,3,4-TETRAHYDRO-6,7-DIALKOXY-3-ISOQUINOLINECARBOXYLIC ACID AND DERIVATIVES

FIELD OF INVENTION

The present invention relates to a commercial process for the production of (S)-1,2,3,4-tetrahydro-6,7-dialkoxy-3-isoquinolinecarboxylic acid compounds (1) and their derivatives from Levodopa (L-Dopa). The ultimately prepared compounds are used as intermediates for, but not limited to, the preparation of substituted derivatives of 1,2,3,4-tetrahydro-6,7-dialkoxy-3-isoquinolinecarboxylic acid such as those described in U.S. Pat. No. 4,344,949.

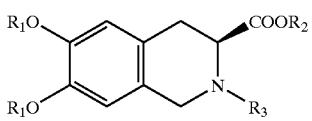

BACKGROUND OF THE INVENTION

The ACE inhibitor moexipril hydrochloride contains the 1,2,3,4-tetrahydro-6,7-dimethoxy-3-isoquinolinecarboxylic acid moiety in its structure, and it is known that the enantiomer possessing the (S) or (L)-configuration is required for optimum ACE inhibitory activity. This is disclosed in U.S. Pat. No. 4,344,949, and in Klutchko, S. et al. *J. Med. Chem.* 1986, 29, pp. 1953–1961 "Synthesis of Novel Angiotensin Converting Enzyme Inhibitor Quinapril and Related Compounds. A Divergence of Structure-Activity Relationships for non-Sulfhydryl and Sulfhydry Types". The prior art synthetic techniques for enantiomerically-enriched 1,2,3,4-tetrahydro-6,7-dimethoxy-3-isoquinolinecarboxylic acid requires an enantiomerically-enriched L-3,4-dimethoxyphenylalanine precursor, which was made by asymmetric hydrogenation of α-amino-3,4-dimethoxycinnamic acid derivatives (O'Reilly, N. J. et al. U.S. Pat. No. 4,912,221) or enzymatic transamination of 3,4-RO(R1O)C$_6$H$_3$CH$_2$CO—CO$_2$H (DE 2148953) or enzymatic/chemical resolution (U.S. Pat. No. 3,669,837, GB 1241405). These approaches have limited commercial use due to cost and the necessity for specialized equipment. Also, the prior art synthetic technique have failed to produce compounds having optical purity levels of over 97% ee. The designation %ee (enantiomeric excess) represents: [(amount of desired isomer−amount of undesired isomer)/total amount of both isomers]×100%. Therefore, an efficient method for preparing enantiomerically-enriched (S)-1,2,3,4-tetrahydro-6,7-dialkoxy-3-isoquinolinecarboxylic acid compounds (1) and their derivatives was needed to overcome the above deficiencies.

SUMMARY OF THE INVENTION

According to an aspect of the present invention there is provided a method for the preparation of (S)-1,2,3,4-tetrahydro-6,7-dialkoxy-3-isoquinolinecarboxylic acid compounds and their derivatives represented by the general formula 1:

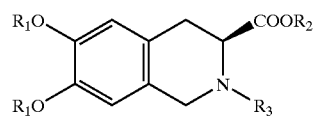

which process comprises reacting Levodopa of formula 2 with formaldehyde or formaldehyde precursors to obtain (S)-1,2,3,4-tetrahydro-6,7-dihydroxy-3-isoquinolinecarboxylic acid of formula 3; protecting the amino group of the compound of formula 3; alkylating the phenol groups of formula 4 to form compound of formula 5; and esterifying the carboxylic acid of formula 5 and optionally removing the N-protecting group.

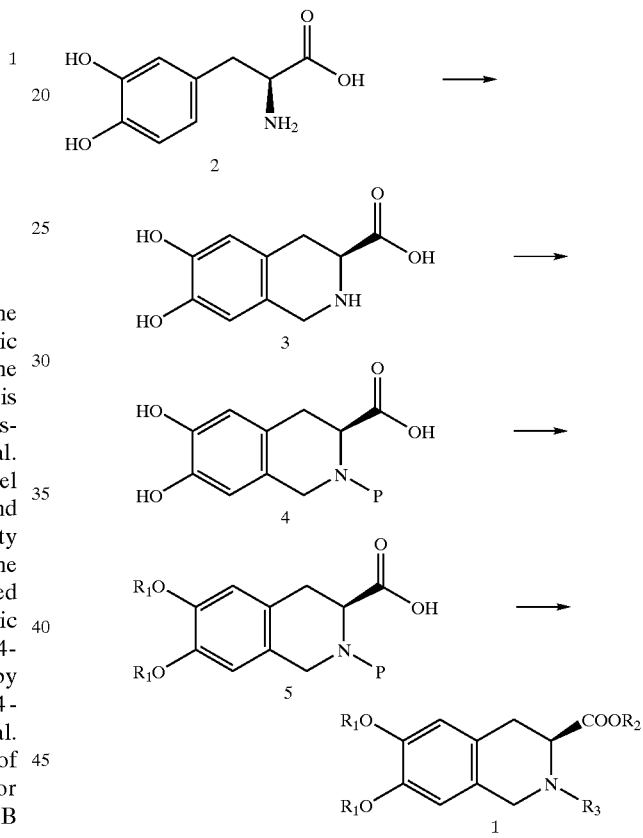

where $R_1$ is hydrogen, lower alkyl, C2–C12 acyl, or $R_1O$ together are methylenedioxy. When $R_1$ is a lower alkyl group, the preferred substituents are those of 1 to 9 carbon atoms. $R_2$ is hydrogen, alkyl, substituted alkyl, alkenyl, substituted alkenyl, aryl, substituted aryl, aralkyl or substituted aralkyl group. When $R_2$ represents an alkyl group, the preferred alkyls are those of 1 to 8 carbon atoms. $R_3$ is hydrogen, C2–C12 acyl group, benzyl, alkoxycarbonyl group, or aralkoxycarbonyl group. The process of instant invention provides an enantiomerically-enriched compound useful for, but not limited to, preparing moexipril and salts thereof. The preferred enantiomerically-enriched compounds obtained by the instant invention are (S)-1,2,3,4-tetrahydro-6,7-dimethoxy-3-isoquinolinecarboxylic acid, (S)-1,2,3,4-tetrahydro-6,7-dimethoxy-3-isoquinolinecarboxylic acid benzyl ester, and (S)-1,2,3,4-tetrahydro-6,7-diethoxy-3-isoquinolinecarboxylic acid. According to a further aspect of the invention, there are provided processes for making moexipril and salts thereof by reacting known compound of formula 9

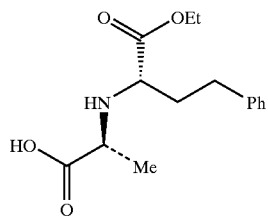

with compound of formula 1 wherein compound of formula 1 is (S)-1,2,3,4-tetrahydro-6,7-dimethoxy-3-isoquinolinecarboxylic acid or (S)-1,2,3,4-tetrahydro-6,7-dimethoxy-3-isoquinolinecarboxylic acid benzyl ester. The coupling of compound (1) prepared according to instant invention with compound of formula 9 may be carried out by traditional method known to those skilled in the art.

The present invention also relates to new intermediate compounds of formulas A and B, useful for, but not limited to, the production of substituted acyl derivatives of tetrahydroisoquinoline carboxylic acids.

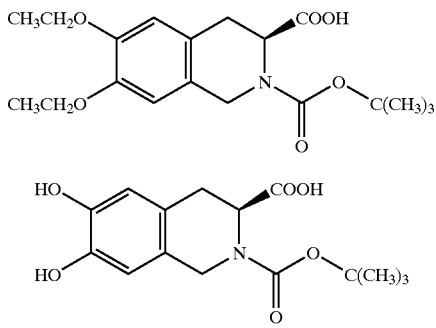

In accordance with the present invention, the (S)-1,2,3,4-tetrahydro-6,7-dialkoxy-3-isoquinolinecarboxylic acid compound (1) and their derivatives are prepared from commercially available and inexpensive material Levodopa (2) (L-Dopa) in high yield.

Surprisingly, the absolute (S)-configuration of Levodopa was transferred to compound (1) after multistep transformation. The starting material Levodopa (2) is a drug used for the treatment of Parkinson's disease, and can be obtained in one step enzymatically from L-tyrosine, which is an inexpensive, readily available amino acid. Scheme 1 outlines the method utilized for the preparation of the compound (1).

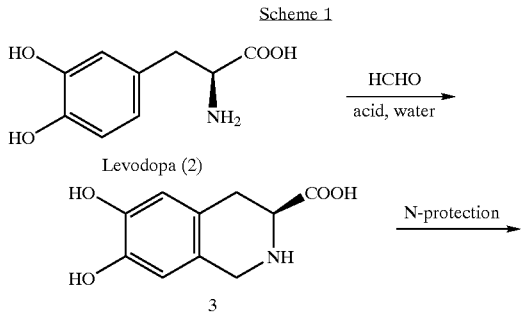

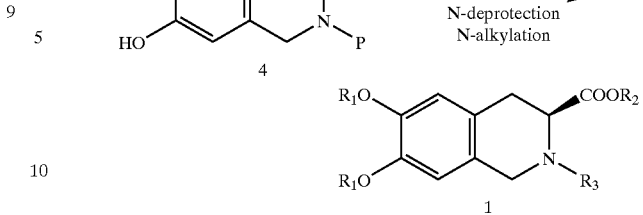

wherein $R_1$, $R_2$, $R_3$ are defined as above. P could be hydrogen or various amino protective groups. For a comprehensive review of amino protective groups, see Greene, T. W. and Wuts, P. G. M., 'Chapter 7. Protection for the Amino Group', in "Protective Groups in Organic Synthesis", Second Edition, John Wiley & Sons, Inc., 1999, pp. 494–653. In this context, the preferred groups are selected from C2–C12 carbonyl group, benzyl, aralkoxy and alkoxycarbonyl groups.

The preparation of (S)-1,2,3,4-tetrahydro-6,7-dihydroxy-3isoquinolinecarboxylic acid (3) comprises reacting its precursor Levodopa (2) with formaldehyde or formaldehyde precursor, for example paraformaldehyde, in the presence of an acid or mixture of acids. [Some Isoquinoline Derivatives" (*J. Org. Chem.* 1961, 26, pp. 3533–3534) and Brossi, A. et al. "'Alkaloids' in Mammalian Tissues. I. Condensation of L-Dopa and its two Mono-O-methyl Ethers with Formaldehyde and Acetaldehyde" (*Helv. Chim. Acta,* 1972, 55, pp.15–21)].

The amino group in compound (3) is protected by amino protective groups, such as carbamates, amides, alkyl, aryl, silyl and sulfenyl derivatives, to form compound (4). The compounds (3) or (4) are then reacted with O-alkylating reagents to produce the compound (1).

The novel process of this invention provides the following advantages:

The overall chemical yield and the procedure is suitable for large scale production and does not require specialized equipment. Starting material Levodopa (2) is commercial available and inexpensive. Levodopa can also be obtained in one step enzymatically from L-tyrosine. The absolute (S)-configuration of Levodopa (2) could be transferred to compound (1) after multistep transformation. If Levodopa is made from L-tyrosine, the chirality of compound (1) ultimately comes from L-tyrosine.

DETAILS OF THE INVENTION

In the present invention, (S)-1,2,3,4-tetrahydro-6,7-dialkoxy-3-isoquinolinecarboxylic acid compounds and their derivatives are prepared from Levodopa with high chemical and optical purity and in good to excellent yield.

Scheme 2 depicts such a process, where $R_1$ is hydrogen, lower alkyl, C2–C12 acyl, or $R_1O$ together are methylenedioxy. When $R_1$ is a lower alkyl group, the preferred substituents are those of 1 to 9 carbon atoms. $R_2$ is hydrogen, alkyl, substituted alkyl, alkenyl, substituted alkenyl, aryl, substituted aryl, aralkyl or substituted aralkyl group. When $R_2$ represents an alkyl group, the preferred alkyls are those of 1 to 8 carbon atoms. $R_3$ is hydrogen, C2–C12 acyl group, benzyl, alkoxycarbonyl group, aralkoxycarbonyl group. P is hydrogen, C2–C12 acyl groups, benzyl, alkoxycarbonyl or aralkoxycarbonyl groups.

Scheme 2

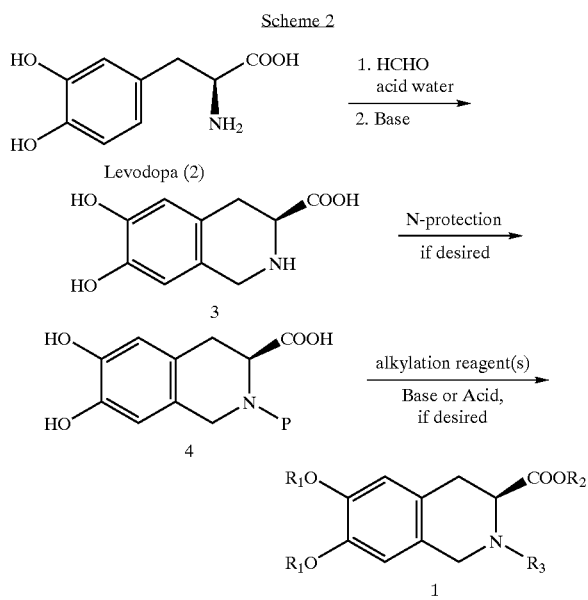

Levodopa (2) is reacted with formaldehyde or formaldehyde precursors, for example paraformaldehyde, in a solution in the presence of an acid or a mixture of the acids, such as hydrochloric acid, sulfuric acid, nitric acid, and the like, to produce (S)-1,2,3,4-tetrahydro-6,7-dihydroxy-3-isoquinolinecarboxylic acid (3).

The protective groups for the protection of the amino moiety in compound (3) is selected from carbamates, amides, alkyl, aryl, silyl, sulfenyl and sulfonyl derivatives. The preferred carbamates are selected from methyl carbamate, ethyl carbamate, t-butyl carbamate, benzyl carbamate, t-amyl carbamate, cyclohexyl carbamate, isobutyl carbamate, and the like. The compound (3) is reacted with alkyl or aryl chloroformate or dialkyl or diaryl dicarbonate in the presence of a base or a mixture of bases in a suitable solvent or solvent mixture. The preferred amides can be selected from N-formyl, N-acetyl, N-benzoyl, N-picolinoyl, N-3-phenylpropionyl, N-4-pentenoyl, N-3-pyridylcarboxamido, and the like. The preferred alkyl, aryl or aralkyl groups are benzyl and its derivative. The preferred N-silyl groups are trimethylsilyl, t-butyldimethylsilyl, t-butyldiphenylsilyl, and the like. The preferred N-sulfenyl and N-sulfonyl groups are benzenesulfenamide, triphenylmethylsulfenamide, p-toluenesulfonamide, benzenesulfonamide, and the like.

Both compounds (3) and (4) can be subjected to O-alkylation by treatment with an alkylating reagent in the presence of a base or a mixture of bases in a suitable solvent or solvent mixture. The alkylation reagents can be selected from alkyl or aryl halides, alkyl and aryl p-toluenesulfonate, alkyl and aryl methanesulfonate, alkyl and aryl trifluromethanesulfonate, dialkyl sulfates, and the like. The preferred reagents include benzyl bromide, benzyl chloride, methyl iodide, methyl bromide, ethyl iodide, ethyl bromide, methyl methanesulfonate, methyl p-toluenesulfonate, dimethyl sulfate, diethyl sulfate, and the like. When $R_1O$ together are methylenedioxy, the alkylation reagents can be selected from dichloromethane, dibromomethane, and the like. The base can be an inorganic or an organic base. The preferred bases are sodium hydroxide, potassium hydroxide, sodium carbonate, sodium bicarbonate, potassium carbonate, potassium bicarbonate, triethylamine, tributylamine, pyridine, and the like.

The carboxylic acid group in compounds (3), (4) and (1) also can be alkylated by reacting the compound with an alcohol or an alkylene in the presence of an acid or a mixture of acids. The preferred alcohols are methanol, ethanol, benzyl alcohol, or the like. The preferred alkylenes are isobutylene, and the like. The acid can be inorganic and organic, such as hydrochloric acid, sulfuric acid, nitric acid, acetic acid, methanesulfuric acid, hydrogen chloride, trimethylsilyl chloride, polylphosphoric acid, p-toluenesulfonic acid, and the like. If necessary, the N-protective group can be removed by standard chemical methods, which have been well described in the prior art.

A more specific method is described in Scheme 3, wherein P is the protective group for the amino group, and is defined as below. $R_1$ is hydrogen, lower alkyl, C2–C12 acyl, or $R_1O$ together are methylenedioxy. When $R_1$ is a lower alkyl group, the preferred substituents are those of 1 to 9 carbon atoms. $R_2$ is hydrogen, alkyl, substituted alkyl, alkenyl, substituted alkenyl, aryl, substituted aryl, aralkyl or substituted aralkyl group. When $R_2$ is an alkyl group, the preferred alkyls are those of 1 to 8 carbon atoms.

Scheme 3

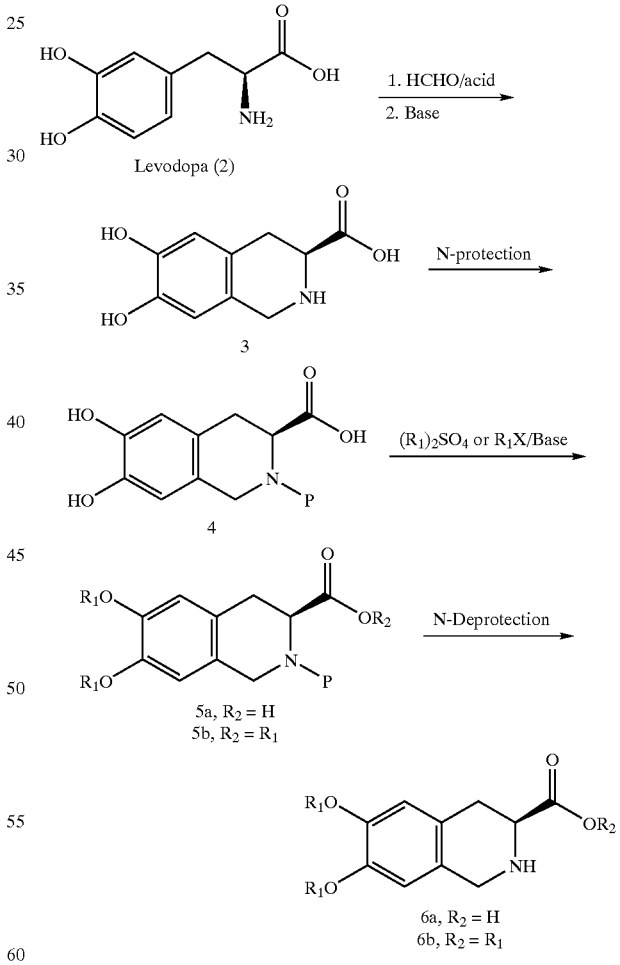

Levodopa (2) is reacted with formaldehyde or formaldehyde precursors, for example paraformaldehyde, in a solution in the presence of an acid or a mixture of the acids, such as hydrochloric acid, sulfuric acid, nitric acid, p-toluenesulforic acid and the like. The concentration of the acid can range from 0.1 N to 10 N. The preferred concentration is from 0.2 N to 2 N. The amount of the acid or acids mixture can range from 0.5 to 10 moles per mole of Levodopa, and the preferred amount is from 1.0 to 3.0 moles per mole of Levodopa. The solvent used in this reaction can be selected from water, alcohols, or mixtures. The temperature of this reaction can range from −50° C. to 100° C. The preferred temperature is 0° C. to 50° C. After complete reaction, the mixture is treated with a base or a mixture of bases, and compound (3) precipitates from the reaction mixture. The product can be collected by filtration. Suitable bases include organic or inorganic base, such as sodium hydroxide, potassium hydroxide, sodium carbonate, sodium bicarbonate, potassium carbonate, potassium bicarbonate, triethylamine, tributylamine, pyridine, and the like. The chemical yield of the reaction ranges from 50% to 100%, and the typical yields range from 80%–99%.

The protective groups (P) for the protection of amino group in compound (3) are selected from carbamates, amides, alkyl, aryl, silyl, sulfenyl and sulfonyl derivatives. After complete reaction, the mixture is treated with an acid or a mixture of acids, and compound (4) is isolated by filtration or solvent extraction.

The resulting compound (4) is treated with an alkylating reagent in the presence of a base or a mixture of bases in a suitable solvent or solvent mixture to alkylate the phenol groups or carboxylic group, or both. The preferred reagents include benzyl bromide, benzyl chloride, methyl iodide, methyl bromide, ethyl iodide, ethyl bromide, methyl methanesulfonate, methyl p-toluenesulfonate, dimethyl sulfate, diethyl sulfate, and the like. When $R_1O$ together are methylenedioxy, the alkylation reagents can be selected from dichloromethane, dibromomethane, and the like. The base can be inorganic or organic. Preferred bases are sodium hydroxide, potassium hydroxide, sodium carbonate, sodium bicarbonate, potassium carbonate, potassium bicarbonate, triethylamine, tributylamine, pyridine, and the like. The solvent used in this reaction can be water, alcohols, ketones, benzene, toluene, ethers, dichloromethane, chloroform, and the like, and their mixtures. The temperature of this reaction can range from −50° C. to 150° C. The preferred temperature range is 0° C. to 100° C.

The amino protective group in compound (5a) or (5b) can be removed by standard deprotection techniques, for example, treatment of (5a) or (5b) with an acid or a base, or hydrogenolysis, to produce (S)-1,2,3,4-tetrahydro-6,7-dialkoxy-3-isoquinolinecarboxylic acid compound (6a) or its ester (6b).

SCHEME 4

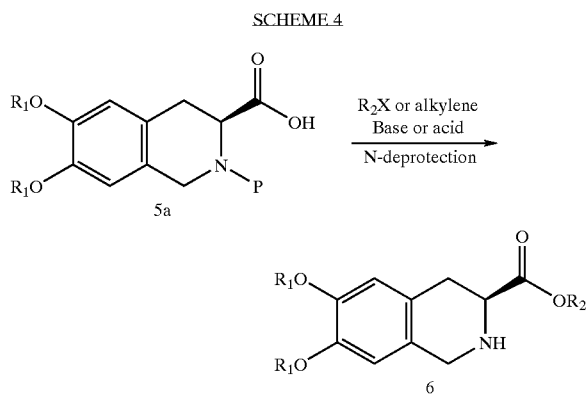

The compound (5a) can also be esterified with an $R_2X$ or an alkylene in the presence of base or acid as described in Scheme 4 to produce (S)-1,2,3,4-tetrahydro-6,7-dialkoxy-3-isoquinolinecarboxylic acid $R_2$ ester 6, wherein $R_2$ is selected from C1–10 alkyl or aryl groups, such as methyl, ethyl, propyl, isopropyl, butyl, benzyl, isobutyl, tert-butyl, and the like. X is selected from chloro, bromo, iodo, hydroxy, p-toluenesulfonate, methanesulfonate, trifluromethanesulfonate, and the like. The preferred alkylenes are isobutylene, and the like. The acid can be an inorganic or organic acid, such as hydrochloric acid, sulfuric acid, nitric acid, acetic acid, methanesulfuric acid, HCl gas, trimethylsilyl chloride, polylphosphoric acid, p- toluenesulfonic acid, and the like. The preferred bases are sodium hydroxide, sodium carbonate, sodium bicarbonate, potassium hydroxide, potassium carbonate, lithium hydroxide, lithium carbonate, triethylamine, tributylamine, isopropyldiethylamine, and the like. The amino protective group could be removed during esterification, or by a separate reaction.

The following non-limiting examples illustrate the process for producing (S)-1,2,3,4-tetrahydro-6,7-dialkoxy-3-isoquinolinecarboxylic acid and derivatives from Levodopa via the processes of the present invention.

EXAMPLE 1

Preparation of (S)-1,2,3,4-tetrahydro-6,7-dihydroxy-3-isoquinolinecarboxylic Acid To a cold (0–5° C.) suspension of Levodopa (197.2 g, 1.0 mol) in water (1.18 L) was added 32% aqueous HCl (159.5 g, 1.4 mol). The resulting solution was cooled to 0–5° C., and 37% formaldehyde water solution (243.24 g, 3.0 mol) was added. The resulting solution was allowed to warm to 20–25° C., and stirred at 20–25° C. for 10 h. The reaction solution was cooled to 0–5° C., and 2 N aqueous NaOH (700 mL, 1.4 mol) was slowly added to adjust pH to 5–5.5. White or light yellow solids precipitated during the addition. The resulting suspension was stirred at 0–5° C. for 2–3 h. The mixture was filtered, and rinsed with water (2×500 mL). The solids were dried under vacuum to give 199.52 g of a light yellow solid. Yield=95.3%.

EXAMPLE 2

Preparation of (S)-1,2,3,4-tetrahydro-6,7-dihydroxy-2-(tert-butyloxycarbonyl)-3-isoquinolinecarboxylic Acid To a cold mixture of (S)-1,2,3,4-tetrahydro-6,7-dihydroxy-3-isoquinolinecarboxylic acid (199.5 g, 0.9536 mol) and water (1.2 L) was added methanol (400 mL) and triethylamine (193 g, 1.91 mol). The mixture was stirred at 0–5° C. and gave a light orange solution. A solution of tert-butyl dicarbonate (218.25 g, 1.0 mol) in methanol (550 mL) was added in portions over 0.5 h. The resulting mixture was stirred at 0–10° C. for 0.5 h, then 20–25° C. overnight (15 h). The reaction mixture then was vacuum distilled at 30–40° C. over 4–6 hours, to 1.3 L. The resulting mixture was cooled, and toluene (200 mL) was added follow by 32% aqueous HCl to adjust reaction mixture pH to 1.5–1.8. Heptane (200 mL) was added and the mixture was stirred at 5–15° C. and yellow solids precipitated. The suspension was filtered, and the solid cake was rinsed with water (2×400 mL). The solids were dried under vacuum at 40° C. to give 280.5 g of a yellow solid. Yield=90.32%. $^1$H NMR (DMSO-$d_6$) δ: 1.38, 1.44 (s, 9H, C(CH$_3$)$_3$), 2.8–3.0 (m, 2H, CH$_2$CHCOOH), 4.12–4.45 (m, 2H, CH$_2$N), 4.56 (dd, J=5.6, 4.3 Hz) and 4.79 (dd, J=5.1, 3.6 Hz, minor rotamer) (1H, CHCOOH), 6.47, 6.50, 6.54 (s, 2H, PhH), 8.78 (br s, 2H, OH), 12.5 (br s, 1H, COOH), KF=5.4%.

EXAMPLE 3

Preparation of (S)-1,2,3,4-tetrahydro-6,7-dimethoxy-2-(tert-butyloxycarbonyl)-3-isoquinolinecarboxylic Acid To a suspension of (S)-1,2,3,4-tetrahydro-6,7-dihydroxy-2-(tert-butyloxycarbonyl)-3-isoquinolinecarboxylic acid (280.5 g, 0.857 mol) in water (280 mL) and acetone (280 mL) was added dimethyl sulfate (356.8 g, 2.828 mol) at 20° C. A solution of 50% aqueous NaOH (226.25 g, 2.828 mol) was added to the reaction mixture in small portions at an internal temperature below 45° C. After complete addition, the cloudy yellow solution was heated to 60° C., and stirred at 60–65° C. Water (1120 mL) and 50% aqueous NaOH solution (102.84 g, 1.286 mol) were added, and the mixture was stirred at 60–65° C. for 1 h. The reaction mixture was cooled to 0–5° C., and toluene (140 mL) and heptane (280 mL) were added followed by 32% aqueous HCl (151.5 g, 1.33 mol). The resulting light yellow suspension was stirred at 5–15° C. for 1 h, then was filtered and the cake was rinsed with heptane/toluene (2:1 v/v) (420 mL) and water (2×420 mL). The damp solids were dried under vacuum at 45° C. for 10–15 h, to give a light yellow solid: 297.5 g. Yield=97.7%. $^1$H NMR (DMSO-d$_6$) δ: 1.39, 1.46 (s, 9H, C(CH$_3$)$_3$), 2.93–3.18 (m, 2H, CH$_2$CHCOOH), 3.17 (s, 6H, OCH$_3$), 4.30 (d, J=16.15 Hz) and 4.37 (d, J=16.40 Hz, minor rotamer) (1H, CHHN), 4.45 (d, J=16.15 Hz) and 4.52 (d, J=16.40 Hz, minor rotamer) (1H, CHHN), 4.68 (dd, J=5.4, 4.3 Hz) and 4.90 (dd, J=5.9, 2.2 Hz, minor rotamer) (1H, CHCOOH), 6.74, 6.78, 6.81 (s, 2H, PhH), KF=5.1%.

EXAMPLE 4

Preparation of (S)-1,2,3,4-tetrahydro-6,7-diethoxy-2-(tert-butyloxycarbonyl)-3-isoquinolinecarboxylic Acid The compound was prepared via the same procedure of example 3, except diethyl sulfate was used instead of dimethyl sulfate. Yield=94%. $^1$H NMR (DMSO-d$_6$) δ: 1.3 (t, 6H, J=7.0 Hz, CH$_2$CH$_3$), 1.39, 1.45 (s, 9H, C(CH$_3$)$_3$), 2.9–3.12 (m, 2H, CH$_2$CHCOOH), 3.97 (q, 4H, CH$_2$CH$_3$), 4.25–4.55 (m, 2H, CH$_2$N), 4.63 (dd, J=5.2, 4.7 Hz) and 4.86 (dd, J=5.9, 2.2 Hz, minor rotamer) (1H, CHCOOH), 6.73, 6.74, 6.79, 6.86 (s, 2H, PhH).

EXAMPLE 5

Preparation of (S)-1,2,3,4-tetrahydro-6,7-dimethoxy-2-(tert-butyloxycarbonyl)-3-isoquinolinecarboxylic Acid, Benzyl Ester Benzyl chloride (116.4 g, 0.92 mol), powdered K$_2$CO$_3$ solids (87 g, 0.63 mol), NaI (6.0 g, 0.04 mol) and Bu$_4$N$^+$Br$^-$ (1.5 g, 0.0046 mol) were added to a solution of crude compound (S)-1,2,3,4-tetrahydro-6,7-dimethoxy-2-(tert-butyloxycarbonyl)-3-isoquinolinecarboxylic acid (297 g, 0.8357 mol) in DMF (890 mL) at 20–25° C. The reaction mixture was stirred at 40–50° C. for 5 h. The reaction mixture then was cooled to 0–5° C., and water (1.78 L) was added in portions (IT<20° C.). The resulting light yellow suspension was stirred at 5–15° C. The mixture was filtered and washed with water (2×600 mL) and heptane (600 mL). The off-white solids were dried under vacuum at 45° C. to afford crude (S)-1,2,3,4-tetrahydro-6,7-dimethoxy-2-(tert-butyloxycarbonyl)-3-isoquinolinecarboxylic acid benzyl ester (335 g, 93.8% yield). $^1$H NMR (DMSO-d$_6$) δ: 1.35, 1.45 (s, 9H, C(CH$_3$)$_3$), 2.93–3.18 (m, 2H, CH$_2$CHCOOH), 3.17 (s, 6H, OCH$_3$), 4.30 (d, J=16.15 Hz) and 4.37 (d, J=16.40 Hz, minor rotamer) (1H, CHHN), 4.45 (d, J=16.15 Hz) and 4.52 (d, J=16.40 Hz, minor rotamer) (1H, CHHN), 4.68 (dd, J=5.4, 4.3 Hz) and 4.90 (dd, J=5.9, 2.2 Hz, minor rotamer) (1H, CHCOOH), 6.74, 6.78, 6.81 (s, PhH).

EXAMPLE 6

Preparation of (S)-1,2,3,4-tetrahydro-6,7-dimethoxy-3-isoquinolinecarboxylic Acid, Benzyl Ester, Hydrochloride (Method A)

To a suspension of crude (S)-1,2,3,4-tetrahydro-6,7-dimethoxy-2-(tert-butyloxycarbonyl)-3-isoquinolinecarboxylic acid benzyl ester (example 5) (335 g, 0.7836 mol) in ethyl acetate (335 mL) and toluene (335 mL) was added 20% HCl solution in IPA (357 g, 1.959 mol) at 15–20° C. The reaction mixture then was heated to 40° C. over 1–2 h, and stirred at this temperature for 2 h. A 20% HCl solution in IPA (71.4 g, 0.3918 mol) was added, and the stirring was continued for another 2 h. The reaction mixture was cooled to 15–20° C., and stirred at this temperature. The mixture was filtered, and washed with ethyl acetate (2×670 mL). The white solids were dried under vacuum at 40° C. to give 278.6 g (99% yield, ee=98%) of (S)-1,2,3,4-tetrahydro-6,7-dimethoxy-3-isoquinolinecarboxylic acid benzyl ester, hydrochloride. $^1$H NMR (DMSO-d$_6$) δ: 3.10 (dd, J=16.64, 10.74 Hz, 1H, CHHCHCOOH), 3.24 (dd, J=16.64, 5.10 Hz, 1H, CHHCHCOOH), 3.72 (s, 6H, OCH$_3$), 4.23 (br s, 2H, CH$_2$N), 4.58 (dd, J=10.74, 5.10 hz, 1H, CHCOOH), 5.27 (d, J=12.48 Hz, 1H, PhCHH), 5.33 (d, J=12.48 Hz, 1H, PhCHH), 6.85 (br s, 2H, PhH), 7.35–7.46 (m, 5H, PhHCH$_2$), 10.19 (br s, 2H, NH.HCl).

EXAMPLE 7

Preparation of (S)-1,2,3,4-tetrahydro-6,7-dimethoxy-3-isoquinolinecarboxylic Acid, Benzyl Ester, Hydrochloride (Method B)

A mixture of (S)-1,2,3,4-tetrahydro-6,7-dimethoxy-2-(tert-butyloxycarbonyl)-3-isoquinolinecarboxylic acid (example 3) (17.8 g, 0.05 mol), benzyl alcohol (27.0 g, 0.25 mol), p-toluenesulfonic acid monohydrate (11.42 g, 0.06 mol) and toluene (100 mL) was refluxed using Dean-Stark apparatus to remove water. The reaction was refluxed, and 2.9 mL of water was collected. The reaction was cooled and 20% HCl/IPA solution (11 g) and methyl tert-butyl ether (90 mL) were added. The resulting white suspension was stirred at room temperature. The mixture was filtered, and rinsed with methyl tert-butyl ether (2×30 mL). The solids were dried under vacuum, to give 16.4 g of (S)-1,2,3,4-tetrahydro-6,7-dimethoxy-3-isoquinolinecarboxylic acid, benzyl ester, hydrochloride as a white solid. Yield=90.2%.

EXAMPLE 8

Preparation of (S)-1,2,3,4-tetrahydro-6,7-diethoxy-3-isoquinolinecarboxylic Acid, Benzyl Ester, Hydrochloride A mixture of (S)-1,2,3,4-tetrahydro-6,7-diethoxy-2-(tert-butyloxycarbonyl)-3-isoquinolinecarboxylic acid (example 4) (18.3 g, 0.05 mol), benzyl alcohol (27.0 g, 0.25 mol), p-toluenesulfonic acid monohydrate (11.42 g, 0.06 mol) and toluene (100 mL) was refluxed using Dean-Stark apparatus to remove water. The reaction was refluxed for 5 hrs, and 2 mL of water was collected. The reaction was cooled to room temperature, and 20% HCl/IPA solution (11 g) was added followed by methyl tert-butyl ether (90 mL). The resulting white suspension was stirred and the mixture was filtered, and rinsed with methyl tert-butyl ether (2×30 mL). The solids were dried under vacuum, to give 16.4 g of (S)-1,2,3,4-tetrahydro-6,7-diethoxy-3-isoquinolinecarboxylic acid, benzyl ester, hydrochloride as a white solid. Yield=84%. $^1$H NMR (DMSO-d$_6$) δ: 1.33 (t, J=6.7 Hz, 6H, CH$_2$CH$_3$), 3.09 (dd, J=16.63, 10.89 Hz, 1H, CHHCHCOOH), 3.23 (dd, J=16.63, 5.0 Hz, 1H, CHHCHCOOH), 3.99 (q, J=6.7 Hz, 4H, CH$_2$CH$_3$), 4.23 (br s, 2H, CH$_2$N), 4.58 (dd, J=10.89, 5.0 Hz, 1H, CHCOOH), 5.28 (d, J=12.54 Hz, 1H, PhCHH), 5.33 (d, J=12.54 Hz, 1H, PhCHH), 6.86 (br s, 2H, PhH), 7.35–7.46 (m, 5H, PhHCH$_2$), 10.30 (br s, 2H, NH.HCl).

EXAMPLE 9

Preparation of (S)-1,2,3,4-tetrahydro-6,7-dimethoxy-3-isoquinolinecarboxylic Acid Hydrochloride To a solution of (S)-1,2,3,4-tetrahydro-6,7-dimethoxy-2-(tert-butyloxycarbonyl)-3-isoquinolinecarboxylic acid (example 3) (60 g, 0.17 mol) in methanol (300 mL) was added 3 N aqueous HCl (240 mL, 0.72 mol). The mixture was heated to 60° C. and stirred at 60° C. for 2 hrs. The clear reaction solution was evaporated under vacuum to 200 mL. The resulting white suspension was then cooled to 0–5° C. and stirred at 0–5° C., filtered, and rinsed with cold water (2×35 mL). The solid was dried under vacuum to give 42 g of (S)-1,2,3,4-tetrahydro-6,7-dimethoxy-3-isoquinolinecarboxylic acid hydrochloride (yield 90.9%, ee>98%). $^1$H NMR (DMSO-d$_6$) δ: 3.06 (dd, J=16.7, 10.8 Hz, 1H, CHHCHCOOH), 3.22 (dd, J=16.7, 4.7 Hz, 1H, CHHCHCOOH), 3.72, 3.73 (s, 6 H, OCH$_3$), 4.21 (br s, 2H, CH$_2$N), 4.32 (dd, J=10.8, 4.7 Hz, 1H, CHCOOH), 6.85, 6.87 (s, 2H, PhH), 10.12 (br s, 2H, NHHCl).

EXAMPLE 10

Preparation of (S)-1,2,3,4-tetrahydro-6,7-diethoxy-3-isoquinolinecarboxylic Acid Hydrochloride A solution of (S)-1,2,3,4-tetrahydro-6,7-diethoxy-2-(tert-butyloxycarbonyl)-3-isoquinolinecarboxylic acid (example 4) (18.3 g, 0.05 mol), 20% HCl/IPA solution (18.3 g, 0.1 mol) in ethyl acetate (100 mL) was stirred at 40° C. for 3 hrs. The resulting suspension was cooled to room temperature, filtered, and rinsed with ethyl acetate (2×30 mL). The solids were dried under vacuum to give 12.1 g of (S)-1,2,3,4-tetrahydro-6,7-diethoxy-3-isoquinolinecarboxylic acid. Yield 81%. $^1$H NMR (DMSO-d$_6$) δ: 1.32 (t, J=6.9 Hz, 6H, CH$_2$CH$_3$), 3.03 (dd, J=16.7, 10.9 Hz, 1H, CHHCHCOOH), 3.21 (dd, J=16.7, 4.9 Hz, 1H, CHHCHCOOH), 3.9–4.06 (m, 2H, CH$_2$CH$_3$), 4.2 (br s, 2H, CH$_2$N), 4.33 (dd, J=10.9, 4.9 Hz, 1H, CHCOOH), 6.84, 6.85 (s, 2H, PhH), 9.96 (br s, 2H, NHHCl).

What is claimed is:

1. A process for preparation of (S)-1,2,3,4-Tetrahydro-6,7-dialkoxy-3-isoquinolinecarboxylic acid compounds and their derivatives of the formula 1

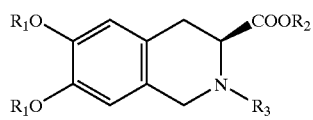

wherein R$_1$ is hydrogen, lower alkyl, C2–C12 acyl, or R$_1$O together are methylenedioxy;

R$_2$ is hydrogen, alkyl, substituted alkyl, alkenyl, substituted alkenyl, aryl, substituted aryl, aralkyl or substituted aralkyl group;

R$_3$ is hydrogen, C2–C12 acyl group, benzyl, alkoxylcarbonyl group, or aralkoxyl carbonyl group;

the process comprising:
(i) reacting Levodopa of formula 2 with formaldehyde or formaldehyde precursors to obtain (S)-1,2,3,4-Tetrahydro-6,7-dihydroxy-3-isoquinolinecarboxylic acid of formula 3;
(ii) protecting the amino group of formula 3;
(iii) alkylating the phenol groups of formula 4 to form compound of formula 5; and
(iv) esterifying the carboxylic acid of formula 5 and optionally removing N-protecting group

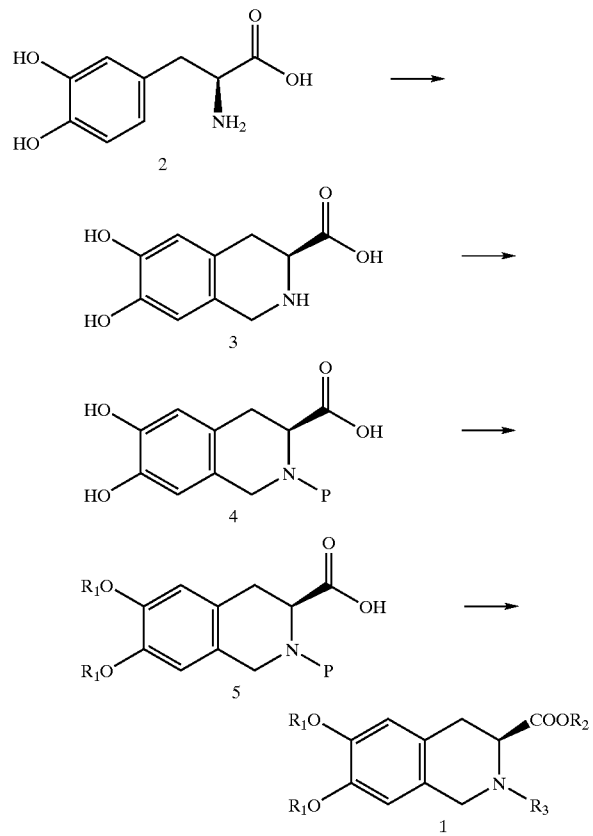

wherein P is alkoxycarbonyl, acyl, alkyl, aryl, silyl, selfenyl or sulfonyl.

2. The process of claim 1 further comprising reacting compound of formula 1 with compound of formula 9 to obtain moexipril or salts thereof:

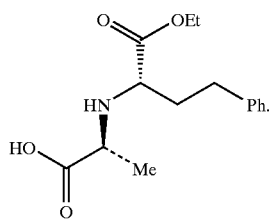

3. The process of claim 1 or 2, wherein the compound of formula 1 is (S)-1,2,3,4-Tetrahydro-6,7-dimethoxy-3-isoquinolinecarboxylic acid.

4. The process of claim 1 or 2, wherein the compound of formula 1 is (S)-1,2,3,4-Tetrahydro-6,7-dimethoxy-3-isoquinolinecarboxylic acid benzyl ester.

5. The process of claim 1, wherein the compound of formula 1 is (S)-1,2,3,4-Tetrahydro-6,7-diethoxy-3-isoquinolinecarboxylic acid.

6. The process of claim 1, wherein the compound of formula 1 is (S)-1,2,3,4-Tetrahydro-6,7-diethoxy-3-isoquinolinecarboxylic acid benzyl ester.

7. A process for preparing compound of formula 5:

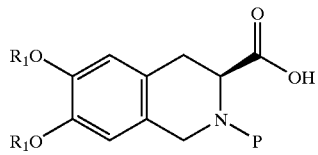

comprising treating compound of formula 4 of claim 1 with an alkylating reagent selected from alkyl or aryl halides, alkyl or aryl p-toluenesulfonate, alkyl or aryl methanesulfonate, alkyl or aryl trifluromethanesulfonate, and dialkyl sulfate, wherein $R_1$ and P are as defined in claim 1.

8. (S)-1,2,3,4-Tetrahydro-6,7-diethoxy-2-(tert-butoxycarbonyl)-3-isoquinoline-carboxylic acid.

9. (S)-1,2,3,4-Tetrahydro-6,7-dihydroxy-2-(tert-butoxycarbonyl)-3-isoquinoline-carboxylic acid.

10. The process of claim 1 or 7 wherein P is tert-butoxycarbonyl, benzyloxycarbonyl, or ethoxycarbonyl.

\* \* \* \* \*